(12) United States Patent
Igata et al.

(10) Patent No.: US 12,709,591 B2
(45) Date of Patent: Aug. 18, 2026

(54) METHOD FOR PRODUCING ACRYLIC ACID

(71) Applicant: NIPPON SHOKUBAI CO., LTD., Osaka (JP)

(72) Inventors: Nao Igata, Himeji (JP); Masaaki Okuno, Himeji (JP); Tatsuya Nakanishi, Himeji (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 905 days.

(21) Appl. No.: 17/758,486

(22) PCT Filed: Jan. 5, 2021

(86) PCT No.: PCT/JP2021/000088
§ 371 (c)(1),
(2) Date: Jul. 7, 2022

(87) PCT Pub. No.: WO2021/145233
PCT Pub. Date: Jul. 22, 2021

(65) Prior Publication Data

US 2022/0402849 A1 Dec. 22, 2022

(30) Foreign Application Priority Data

Jan. 14, 2020 (JP) ................................ 2020-003870

(51) Int. Cl.
*C07C 51/25* (2006.01)

(52) U.S. Cl.
CPC ................................ *C07C 51/252* (2013.01)

(58) Field of Classification Search
CPC ........ C07C 51/252; C07C 57/04; B01J 23/28; B01J 23/8877; B01J 23/885; B01J 21/12
See application file for complete search history.

(56) References Cited

U.S. PATENT DOCUMENTS

2003/0125580 A1 7/2003 Yunoki
2005/0176995 A1 8/2005 Yunoki et al.

FOREIGN PATENT DOCUMENTS

CN 1408700 A 4/2003
EP 1295636 B1 * 10/2008 ........... B01J 23/002
(Continued)

OTHER PUBLICATIONS

Office Action for the corresponding Taiwanese patent application No. 110100653, dated Aug. 11, 2022, with English translation.
(Continued)

*Primary Examiner* — Yate' K Cutliff
(74) *Attorney, Agent, or Firm* — LUCAS & MERCANTI, LLP

(57) ABSTRACT

A method includes supplying a gas containing acrolein to a fixed bed reactor including a reaction tube to produce acrylic acid by vapor phase catalytic oxidation of acrolein. The reaction tube is packed with catalysts having different activities in such a way that catalyst layers are formed in a tube axis direction. A catalyst X having the highest activity among the catalysts contained in all the catalyst layers is placed in the whole or a part of a section up to 30% of a length of all the catalyst layers from a rearmost portion on a gas outlet side toward a gas inlet side. A catalytically active component x in the catalyst X has Mo, V, and optionally Cu. When Cu is included, its amount is 0.8 mol or less per 12 mol of Mo. A specific surface area of the catalytically active component x is 15-40 $m^2/g$.

3 Claims, 2 Drawing Sheets

(56) References Cited

FOREIGN PATENT DOCUMENTS

| | | | | |
|---|---|---|---|---|
| JP | H05-213813 A | | 8/1993 | |
| JP | H07-10802 A | | 1/1995 | |
| JP | 2003-089671 A | | 3/2003 | |
| JP | 2005-224660 A | | 8/2005 | |
| TW | 200712046 A | | 4/2007 | |
| TW | 201219365 A | | 5/2012 | |
| TW | I680801 B | | 1/2020 | |
| WO | WO-2006091005 A1 | * | 8/2006 | ............ B01J 23/002 |

OTHER PUBLICATIONS

Chinese Patent Office, "Second Review Opinion Notice" dated Jan. 5, 2024, which was issued for the corresponding Chinese Patent Application No. 202180009365.9, with English translation, 12 pages.

Office Action dated May 19, 2023 for the corresponding Chinese patent application No. 202180009365.9 with English translation.

PCT, International Search Report for the corresponding patent application No. PCT/JP2021/000088, dated Mar. 16, 2021, with English translation.

* cited by examiner

[Fig. 1]
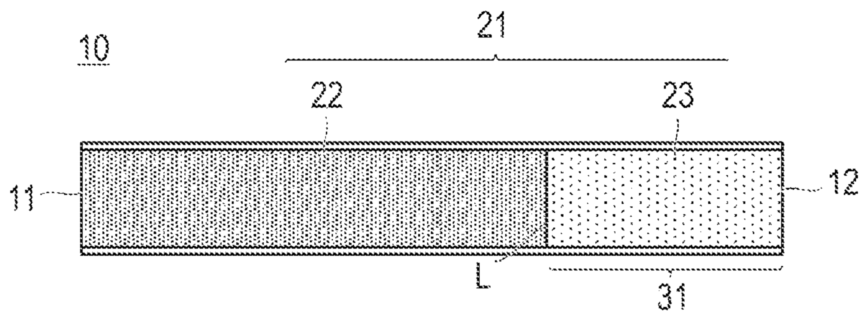

[Fig. 2]
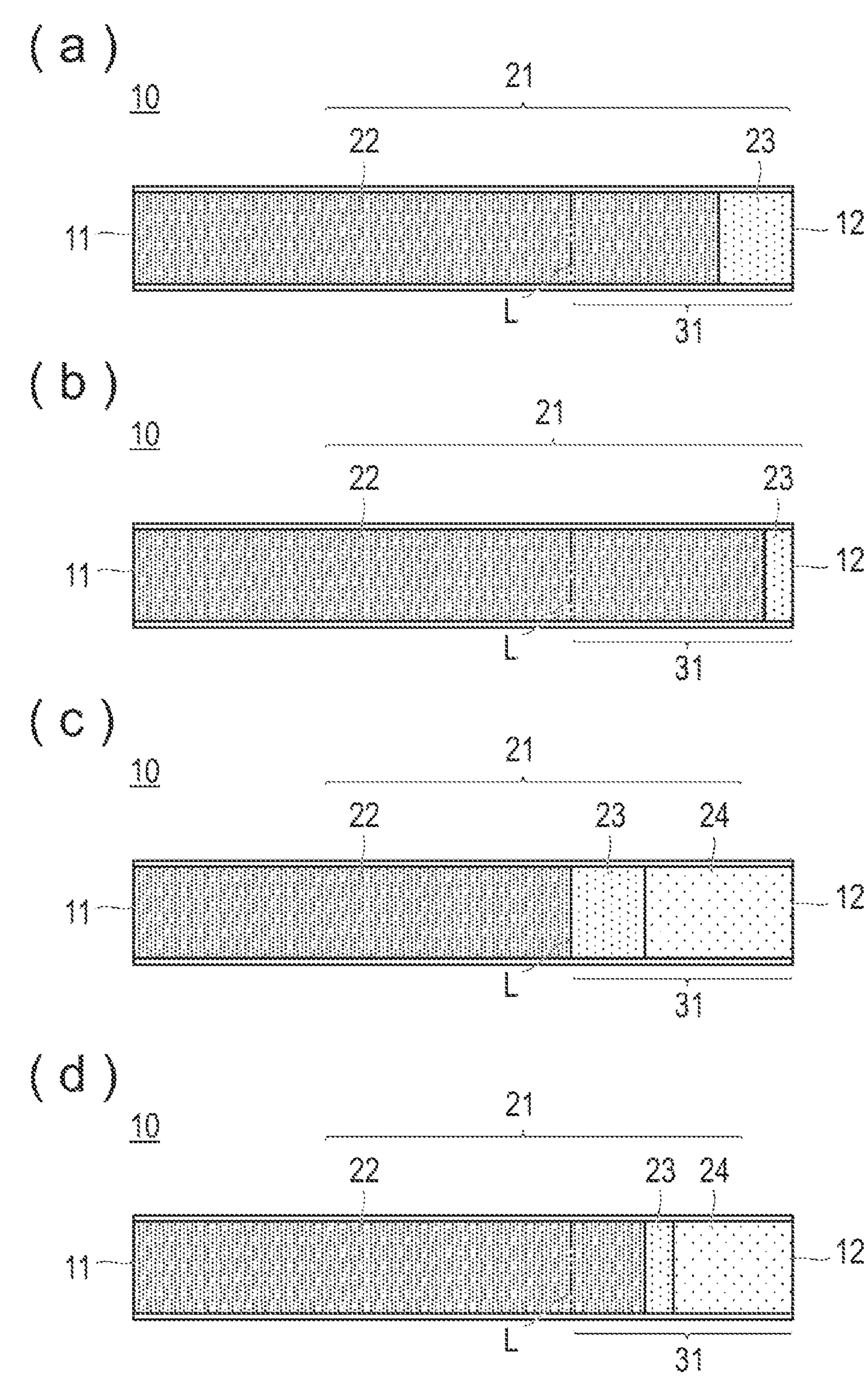

METHOD FOR PRODUCING ACRYLIC ACID

CROSS REFERENCE TO RELATED APPLICATION

This Application is a 371 of PCT/JP2021/000088 filed on Jan. 5, 2021 which, in turn, claimed the priority of Japanese Patent Application No. 2020-003870 filed on Jan. 14, 2020, and the above application is incorporated herein by reference.

TECHNICAL FIELD

The present invention relates to a method for producing acrylic acid.

BACKGROUND ART

A large number of proposals have been made regarding a catalyst used in the production of acrylic acid by vapor phase catalytic oxidation of acrolein. For example, Patent Literatures 1 and 2 disclose a method for producing acrylic acid using a fixed bed multitubular reactor in which a reaction tube is packed with a catalyst composed of an inert support and a catalytically active substance containing molybdenum and vanadium supported thereon. Specifically, Patent Literatures 1 and 2 disclose a method for producing acrylic acid using a reactor in which catalysts are sequentially packed in such a way that the catalytic activity becomes higher from the reactant gas inlet side toward the gas outlet side of the reaction tube.

CITATION LIST

Patent Literature

Patent Literature 1: JPA H07-10802
Patent Literature 2: JPA 2003-89671

SUMMARY OF INVENTION

Technical Problem

It is possible to carry out reaction for a long time while maintaining a high acrylic acid yield, under conditions where the acrolein concentration in the reactant gas is low as in the methods of Literatures 1 and 2 above. However, in recent years, in order to increase the production of acrylic acid, the reaction is carried out in some cases under high load conditions such as an increased acrolein concentration in the reactant gas or an increased space velocity. In general, the higher the load, the higher the reaction temperature. Thus there is room for improvement in the yield of acrylic acid and the catalyst life in the methods of Literatures 1 and 2 above under such high load conditions. In particular, under conditions where the acrolein concentration is high, a local abnormally high temperature zone is likely to be generated in the first half of the catalyst layer, and thus it is difficult to maintain the yield of acrylic acid and the catalyst life.

Therefore, an object of the present invention is to provide a method for producing acrylic acid which can improve the yield of acrylic acid and extend the life of a catalyst, in the method for producing acrylic acid by vapor phase catalytic oxidation of acrolein.

Solution to Problem

The present inventors have made extensive studies in order to solve the above problem. As a result, the present inventors have found that the above problem can be solved by a method for producing acrylic acid, comprising supplying a gas containing acrolein to a fixed bed reactor including a reaction tube to produce acrylic acid by vapor phase catalytic oxidation of acrolein, wherein the reaction tube is packed with catalysts having different activities in such a way that two or more catalyst layers are formed in a tube axis direction of the reaction tube; a catalyst X having the highest activity among the catalysts contained in all the catalyst layers is placed in the whole or a part of a section up to 30% of the length of all the catalyst layers from the rearmost portion on the gas outlet side toward the gas inlet side of all the catalyst layers; a catalytically active component x in the catalyst X has Mo (molybdenum), V (vanadium), and optionally Cu (copper), and when Cu is included, the amount thereof is 0.8 mol or less per 12 mol of Mo; and the specific surface area of the catalytically active component x is 15 $m^2/g$ to 40 $m^2/g$.

Advantageous Effects of Invention

According to the present invention, a high acrolein conversion rate can be obtained at a low reaction temperature even under a high load condition, in a method for producing acrylic acid by vapor phase catalytic oxidation of acrolein. In addition, according to the present invention, there is provided a method for producing acrylic acid which can extend the life of a catalyst and develop a high acrylic acid yield even under a high load condition.

BRIEF DESCRIPTION OF DRAWINGS

FIG. 1 is a schematic diagram illustrating one embodiment of catalyst layers packed in a reaction tube of a fixed bed reactor.

FIG. 2 is schematic diagrams illustrating other embodiments of catalyst layers packed in a reaction tube of a fixed bed reactor.

DESCRIPTION OF EMBODIMENTS

Hereinafter, embodiments of the present invention will be described, and the present invention is not limited only to the following embodiments. In addition, as used herein, "X to Y" indicating a range means "X or more and Y or less."

The method for producing acrylic acid according to the present invention is a method for producing acrylic acid, comprising supplying a gas containing acrolein to a fixed bed reactor including a reaction tube to produce acrylic acid by vapor phase catalytic oxidation of acrolein, wherein the reaction tube is packed with catalysts having different activities in such a way that two or more catalyst layers are formed in a tube axis direction of the reaction tube; a catalyst X having the highest activity among the catalysts contained in all the catalyst layers is placed in the whole or a part of a section up to 30% of the length of all the catalyst layers from the rearmost portion on the gas outlet side toward the gas inlet side of all the catalyst layers; a catalytically active component x in the catalyst X has Mo (molybdenum), V (vanadium), and optionally Cu (copper), and when Cu is included, the amount thereof is 0.8 mol or less per 12 mol of Mo; and the specific surface area of the catalytically active component x is 15 $m^2/g$ to 40 $m^2/g$.

In the present invention, acrylic acid is produced by vapor phase catalytic oxidation of acrolein in the presence of molecular oxygen using a fixed bed reactor equipped with one or more reaction tubes. The term "in the presence of molecular oxygen" as used in the present invention may be defined as being in a state where at least molecular oxygen is present, and the vapor phase catalytic oxidation in the presence of molecular oxygen may be carried out with molecular oxygen alone or a molecular oxygen-containing gas.

The reaction tube in the fixed bed reactor is packed with catalysts having different activities in such a way that two or more catalyst layers are formed in a tube axis direction of the reaction tube. As used herein, two or more catalyst layers packed in the reaction tube of the fixed bed reactor above in the method for producing acrylic acid according to the present invention are collectively referred to as "all the catalyst layers." In the method for producing acrylic acid according to the present invention, a gas containing acrolein (hereinafter, also referred to as an "acrolein-containing gas") as a reactant gas is supplied from the gas inlet side of all the catalyst layers, and the reactant gas after the vapor phase catalytic oxidation reaction is discharged from the gas outlet side. That is, the acrolein-containing gas passes through all the catalyst layers, whereby vapor phase catalytic oxidation is carried out.

In the present invention, a catalyst X having the highest activity among the catalysts contained in all the catalyst layers is placed in the whole or a part of a section up to 30% of the length of all the catalyst layers from the rearmost portion on the gas outlet side toward the gas inlet side in all the catalyst layers. That is, the present invention is characterized in that the catalyst X having the highest activity among the catalysts contained in the two or more catalyst layers (all the catalyst layers) is present in the whole or a part of a specific section on the gas outlet side (rear portion side) of all the catalyst layers. The "activity" in the present invention means the conversion rate of the reactant gas (that is, acrolein). Specifically, by measuring the conversion rate of acrolein when an acrolein-containing gas is supplied to a catalyst layer containing a single catalyst (that is, a single layer) under a certain condition, the activity of the catalyst can be evaluated. Therefore, by changing the type of a catalyst to be packed and determining the acrolein conversion rate under the same condition, the differences in activity of different catalysts can be compared and evaluated.

The method for evaluating the activity of a catalyst, that is, the method for evaluating the activity of a catalyst by measuring the conversion rate of acrolein is not particularly limited, and the conditions of a usually known catalytic activity test method can be applied. The activity is evaluated under one specific condition in the Examples described later, but in the present invention, the activity evaluation conditions can be appropriately set within the following ranges, for example.

Reaction tube length: 200 mm to 500 mm

Reaction tube inner diameter: 10 mm to 30 mm

Catalyst layer length: 50 mm to 150 mm

Gas composition: acrolein: 2 to 5% by volume, oxygen: 5 to 10% by volume, and water vapor: 20 to 50% by volume Space velocity (SV): 1500 $h^{-1}$ to 2500 $h^{-1}$ Reaction temperature: 210° C. to 240° C.

Reaction pressure: 0.10 MPa to 0.15 MPa

Analysis method: The concentrations of acrolein and nitrogen in a gas discharged from the gas outlet side of the reaction tube 2 to 5 hours after the start of gas flow are analyzed by gas chromatography.

The catalyst X includes a catalytically active component x. The catalytically active component x has Mo, V, and optionally Cu, and when Cu is included, the amount thereof is 0.8 mol or less per 12 mol of Mo. That is, the catalytically active component x in the catalyst X does not include Cu, or even if Cu is included, it is 0.8 mol or less per 12 mol of Mo (hereinafter, this form is also referred to as "contain no or a small amount of Cu"). In addition, the catalytically active component x has a specific surface area of 15 $m^2/g$ to 40 $m^2/g$ (hereinafter, also referred to as a "particular specific surface area"), and the catalyst X including the catalytically active component x has the highest activity among the catalysts present in all the catalyst layers. The present inventors have found that it is possible to improve the yield of acrylic acid and extend the life of a catalyst by placing a catalyst X having the highest activity in all the catalyst layers, which contains no or a small amount of Cu and includes a catalytically active component x having a particular specific surface area, in the whole or a part of a specific section on the gas outlet side of all the catalyst layers. The reason why the above advantageous effects are exhibited by the configuration of the present invention is not necessarily clear, but it is considered as follows.

When acrylic acid is produced by vapor phase catalytic oxidation of acrolein (hereinafter, sometimes also referred to as "production of acrylic acid from acrolein"), the following two side reactions occur in addition to the reaction of generating acrylic acid from acrolein as the main purpose: (1) a side reaction in which carbon dioxide, carbon monoxide, acetic acid, and the like are generated by combustion of acrolein or the like (hereinafter, referred to as "side reaction 1 (combustion reaction of acrolein)"), and (2) a side reaction in which carbon dioxide, carbon monoxide, acetic acid, and the like are generated by combustion of acrylic acid or the like (hereinafter, referred to as "side reaction 2 (combustion reaction of acrylic acid)"). Accordingly, it is considered that suppressing these two side reactions can increase the acrylic acid selectivity and improve the yield.

When a catalyst including Cu as a catalytically active component (hereinafter, sometimes also referred to as a "catalyst including Cu") is used in the production of acrylic acid from acrolein, the present inventors have carefully examined how the occurrence of the above side reactions 1 and 2 change focusing on the content of Cu in the catalyst, and as a result found that as the amount of Cu in the catalyst increases, side reaction 1 (combustion reaction of acrolein) decreases whereas side reaction 2 (combustion reaction of acrylic acid) increases. From this, the present inventors have presumed that Cu may suppress side reaction 1 (combustion reaction of acrolein) whereas Cu may promote side reaction 2 (combustion reaction of acrylic acid) and carried out a diligent study based on this presumption.

Here, in the latter half of the catalyst layer, acrolein is almost converted to acrylic acid, and thus the concentration thereof in the gas is low whereas the concentration of acrylic acid in the gas is high. That is, in the latter half of the catalyst layer, it is more important to suppress side reaction 2 (combustion reaction of acrylic acid) than to suppress side reaction 1 (combustion reaction of acrolein) in order to improve the yield of acrylic acid. Accordingly, it is presumed that in the method for producing acrylic acid according to the present invention, placing a catalyst having a low Cu content (that is, a catalyst X containing no or a small amount of Cu as the catalytically active component x) in the latter half of the catalyst layer suppresses the combustion of acrylic acid in the latter half of the catalyst layer and improves the yield of acrylic acid.

In addition, in the method for producing acrylic acid according to the present invention, the catalytically active component x included in the catalyst X has a particular specific surface area. The specific surface area of the catalytically active component x is closely related to the catalytic activity and the likelihood of the side reactions; and in general, the larger the specific surface area, the higher the catalytic activity. However, if the specific surface area is excessively large, the side reactions increase. Since the catalytically active component x of the catalyst X placed in the latter half of the catalyst layer has a particular specific surface area, the present invention can promote the reaction of generating acrylic acid in the latter half of the catalyst layer and suppress the accompanying side reactions, to thereby further enhance the advantageous effects of the present invention.

In the method of producing acrylic acid by vapor phase catalytic oxidation of acrolein, a local abnormally high temperature zone may occur in the first half of the catalyst layer having a high acrolein concentration and this may accelerate the thermal degradation of the catalyst. In such a case, for example, by lowering the reaction temperature, the temperature rise in the catalyst layer can be suppressed and the occurrence of an abnormally high temperature portion can be suppressed; however, on the other hand, the conversion rate of acrolein decreases, and thus as a result the acrylic acid yield decreases. In the method for producing acrylic acid according to the present invention, the reaction temperature can be lowered by placing the catalyst X which has high activity, contains no or a small amount of Cu, and has a particular specific surface area in the latter half of the catalyst. That is, while suppressing the temperature rise in the first half of the catalyst layer, it is possible to convert a large amount of unreacted acrolein into acrylic acid by the highly active catalyst in the latter half of the catalyst layer, where the temperature rise is unlikely to occur. It is presumed that as a result, the abnormal temperature rise in the first half of the catalyst layer was suppressed and also that the catalyst life was improved while maintaining a high acrylic acid yield. However, such a mechanism is merely a presumption and it goes without saying that this does not limit the technical scope of the present invention.

First, a specific section on the gas outlet side of all the catalyst layers in which the catalyst X is present, that is, a section up to 30% of the length of all the catalyst layers from the rearmost portion on the gas outlet side toward the gas inlet side will be described based on FIG. 1 and FIG. 2. FIG. 1 and FIG. 2 is each a schematic diagram illustrating one embodiment of catalyst layers packed in a reaction tube 10 of a fixed bed reactor. As illustrated in FIG. 1, for producing acrylic acid of the present invention, a plurality of catalysts are packed in the reaction tube 10 of the fixed bed reactor to form all the catalyst layers 21. An acrolein-containing gas is supplied to the reaction tube 10 of the fixed bed reactor from the catalyst layer foremost end 11, the supplied acrolein-containing gas passes through all the catalyst layers 21, and the gas after the reaction is discharged from a catalyst layer rearmost end 12. Hereinafter, the catalyst layer foremost end 11 side is also referred to as the gas inlet side, and the catalyst layer foremost end 11 is also referred to as the foremost portion on the gas inlet side of all the catalyst layers. The catalyst layer rearmost end 12 side is also referred to as the gas outlet side, and the catalyst layer rearmost end 12 is also referred to as the rearmost portion on the gas outlet side of all the catalyst layers.

In the embodiment shown in FIG. 1, all the catalyst layers 21 in the reaction tube 10 of the fixed bed reactor is composed of a catalyst layer 22 including a different type of a catalyst from the catalyst X and a catalyst layer 23 including the catalyst X. Here, in FIG. 1, the catalyst layer 23 including the catalyst X is placed in a section 31 up to 30% of the length of all the catalyst layers 21 (hereinafter, simply also referred to as a "section 31") from the catalyst layer rearmost end 12 toward the gas inlet side. The embodiment of FIG. 1 is an embodiment in which the catalyst layer 23 including the catalyst X is placed in the whole of the section 31 up to 30% of the length of all the catalyst layers from the catalyst layer rearmost end 12 toward the gas inlet side. That is, in the embodiment of FIG. 1, the section 31 is composed of a catalyst layer 23 including a catalyst X from the end L of the section 31 to the rearmost end 12 of the catalyst layer.

In the present invention, the catalyst layer 23 including the catalyst X may be placed in a part of the section 31 up to 30% of the length of all the catalyst layers 21 from the catalyst layer rearmost end 12 toward the gas inlet side. For this case, the embodiment in which the catalyst layer 23 including the catalyst X is placed will be described based on FIG. 2. In FIG. 2(*a*), the catalyst layer 23 including the catalyst X is placed in a section, of the section 31, up to 10% of the length of all the catalyst layers 21 from the catalyst layer rearmost end 12 toward the gas inlet side. In FIG. 2(*b*), the catalyst layer 23 including the catalyst X is placed in a section, of the section 31, up to 3% of the length of all the catalyst layers 21 from the catalyst layer rearmost end 12 toward the gas inlet side. In FIG. 2(*c*), the catalyst layer 23 including the catalyst X is placed in a section, of the section 31, up to 10% of the length of all the catalyst layers 21 from the gas inlet side toward the gas outlet side. In FIG. 2(*d*), the catalyst layer 23 including the catalyst X is placed in a section up to 3% of the length of all the catalyst layers 21, which is located in a middle portion of the section 31. In FIG. 2(*c*) and FIG. 2(*d*), a catalyst layer 24 including a catalyst of a type different from that of the catalyst X is placed, adjacent to the catalyst layer 23 including the catalyst X, on the outlet side of the catalyst layer 23 including the catalyst X.

FIG. 2(*a*) and FIG. 2(*b*) are embodiments in which the catalyst layer 23 including the catalyst X is placed in the rearmost portion of the section 31 (that is, the rearmost portion of all the catalyst layers 21), FIG. 2(*c*) is an embodiment in which the catalyst layer 23 including the catalyst X is placed in the foremost portion of the section 31, and FIG. 2(*d*) is an embodiment in which the catalyst layer 23 including the catalyst X is placed in a middle portion of the section 31. In the present invention, the catalyst layer 23 including the catalyst X may be placed in any portion of the section 31, as illustrated in FIG. 2(*a*) to FIG. 2(*d*).

The length of all the catalyst layers 21 means the distance from the catalyst layer foremost end 11 to the catalyst layer rearmost end 12 in a direction parallel to the tube axis, and at this time can be determined by calculating the distance between the catalysts located at both ends of all the catalyst layers 21. The "length of the catalyst layer" may also be referred to as "layer length" or "layer height."

Here, a method for measuring the layer length of the catalyst layer packed in the reaction tube may include using a measure, for example. Specifically, (1) in a reaction tube placed in such a way that the tube axis is parallel to the vertical direction in an empty state before packing a catalyst, a stopper such as a perforated plate is placed at a predetermined position in the reaction tube (for example, a position corresponding to the catalyst layer foremost end 11 in FIG. 1) in such a way as to be perpendicular to the tube axis direction; (2) the distance (space length) D1 from the upper opening of the reaction tube (for example, a position corresponding to the catalyst layer rearmost end 12 in FIG. 1)

to the upper surface of the perforated plate serving as the bottom is measured; (3) thereafter, the catalyst is packed and then the distance (space length) D2 from the upper opening of the reaction tube to the top of the catalyst is measured; and (4) the layer length of the catalyst layer composed of the packed catalyst is calculated by subtracting D2 from D1. When packing other catalysts sequentially, the operations of (2) to (4) may be carried out at the time of packing each catalyst, only except that the already packed catalyst layer is regarded as the "upper surface of the perforated plate" in (2). Thus, the layer length of each catalyst layer and the layer length of all the catalyst layers can be calculated. The distance D1 and the distance D2 are measured in parallel with the tube axis direction of the reaction tube. At this time, the average values obtained by measurement at several points (for example, three points) may be used as the distance D1 and the distance D2. The number of measurement points may be equal to or more than a statistically confidential number.

In a preferable embodiment of the present invention, the layer length of the catalyst layer 23 including the catalyst X is 3 to 30% of the length of all the catalyst layers 21. In a more preferable embodiment, the catalyst layer 23 including the catalyst X is placed in the rearmost portion of all the catalyst layers 21 (embodiments of FIG. 1, FIG. 2(*a*), and FIG. 2(*b*)). Accordingly, preferably, the catalyst layer 23 including the catalyst X and having a layer length of 3 to 30% of the length of all the catalyst layers 21 is placed in the rearmost portion of all the catalyst layers 21. More preferably, the catalyst layer 23 including the catalyst X and having a layer length of 5 to 25%, 5 to 20%, 5 to 15%, or 6 to 10% of the length of all the catalyst layers 21 is placed in the rearmost portion of all the catalyst layers 21. Due to the above configuration, the advantageous effects of the present invention can be further exerted.

The catalyst layer 23 including the catalyst X may also be present in a section other than the section 31 as long as it is placed in any portion of the section 31. Accordingly, examples of a disposition pattern of the catalyst of the present invention also include a pattern in which the catalyst layers 23 including the catalyst X are placed in any portion of the section 31 and any portion on the inlet side than the end L of the section 31 and; and a pattern in which the catalyst layer 23 including the catalyst X is placed in a section up to 40% of the length of all the catalyst layers 21 from the catalyst layer rearmost end 12 toward the gas inlet side.

The catalyst X contains no or a small amount of Cu, and thus the combustion reaction of acrolein may increase. Because of this, when the catalyst layer 23 including the catalyst X is placed beyond the section 31 toward the gas inlet side, the catalyst layer 23 including the catalyst X is preferably placed in a section up to 35% of the length of all the catalyst layers and more preferably placed in a section up to 33% of the length of all the catalyst layers, from the catalyst layer rearmost end 12 toward the gas inlet side. In this case, the advantageous effects of the present invention can be sufficiently exerted.

Next, the features of the catalyst X will be described.

The catalyst X includes a catalytically active component x. The catalytically active component x has Mo, V, and optionally Cu, and when Cu is included, the amount thereof is 0.8 mol or less per 12 mol of Mo, and the specific surface area of the catalytically active component x is 15 $m^2/g$ to 40 $m^2/g$. If the catalyst X including the catalytically active component x having such features is present in the whole or a part of a specific section, acrylic acid can be produced in high yield over a long period of time.

Here, in a preferable embodiment, the composition of the catalytically active component x is represented by the following general formula (1) (provided that oxygen in an oxidation state is omitted):

$$Mo_{12}Cu_aV_bA_cB_dC_eD_fE_g \quad (1)$$

wherein Mo is molybdenum, Cu is copper, V is vanadium, A is at least one element selected from niobium, tungsten, and tantalum, B is at least one element selected from antimony and tellurium, C is at least one element selected from chromium, manganese, iron, cobalt, nickel, zinc, bismuth, tin, thallium, and a rare earth element, D is at least one element selected from an alkali metal and an alkaline earth metal, E is at least one element selected from silicon, aluminum, titanium, zirconium, and cerium, and a, b, c, d, e, f, and g represent the numbers of atoms of Cu, V, A, B, C, D, and E, respectively, and $0 \le a \le 0.8$, $2 \le b \le 10$, $0 \le c \le 12$, $0 \le d \le 6$, $0 \le e \le 12$, $0 \le f \le 5$, and $0 \le g \le 50$. Note that c, d, e, f, and g are the total numbers of atoms of elements represented by A, B, C, and D, respectively.

In the formula (1), a is $0 \le a \le 0.8$, preferably $0 \le a < 0.8$, and more preferably $0 \le a \le 0.6$. That is, the amount of Cu in the catalytically active component x is preferably less than 0.8 mol and more preferably 0.6 mol or less, and may be 0.5 mol or less, 0.4 mol or less, 0.3 mol or less, 0.2 mol or less, or 0.1 mol or less, per 12 mol of Mo. If the amount of Cu exceeds 0.8 mol per 12 mol of Mo, the acrylic acid produced is further combusted as described above, which is not preferable.

In the formula (1), c is preferably $0 \le c \le 3.0$, more preferably $0 \le c \le 2.5$, further preferably $0 \le c \le 2.0$, and further more preferably $0 \le c \le 1.5$. That is, the amount of A in the catalytically active component x is preferably 0 mol or more and 3.0 mol or less, more preferably 0 mol or more and 2.5 mol or less, further preferably 0 mol or more and 2.0 mol or less, and further more preferably 0 mol or more and 1.5 mol or less, per 12 mol of Mo.

In one embodiment of the present invention, in the formula (1), the catalytically active component x may or may not include tungsten (W). In this case, A in the formula (1) is at least one element selected from niobium, tungsten, and tantalum, and c for A (Ac) is $0 \le c \le 12$ and c for W (here, for convenience, represented by "c'") (Wc') is $0 \le c' \le 3.0$. c' is more preferably $0 \le c' \le 2.5$, further preferably $0 \le c' \le 2.0$, and further more preferably $0 \le c' \le 1.5$. That is, the amount of W in the catalytically active component x is preferably 0 mol or more and 3.0 mol or less, more preferably 0 mol or more and 2.5 mol or less, further preferably 0 mol or more and 2.0 mol or less, and further more preferably 0 mol or more and 1.5 mol or less, per 12 mol of Mo.

In one embodiment of the present invention, the catalytically active component x may be in a form including Cu, a form including W, or a form including Cu and W.

For example, in the case of the form in which the catalytically active component x includes Cu, the lower limit of a in the formula (1) is preferably $0 < a$, more preferably $0.1 \le a$, and further more preferably $0.2 \le a$. That is, the amount of Cu in the catalytically active component x is preferably more than 0 mol, more preferably 0.1 mol or more, and further preferably 0.2 mol or more, per 12 mol of Mo. In this case, the amount of Cu in the catalytically active component x is preferably less than 0.8 mol and more preferably 0.6 mol or less, and may be 0.5 mol or less, 0.4 mol or less, or 0.3 mol or less, per 12 mol of Mo. According to the present invention, even with the form in which the catalytically active component x includes Cu, Cu suppresses the combustion reaction of acrolein, and thus it is possible to improve the yield of acrylic acid and extend the life of the catalyst.

In the case of the form in which the catalytically active component x includes W, A in the formula (1) includes tungsten (W). In this case c for A (Ac) is $0<c\leq12$ and c' for W (Wc') is $0<c'\leq3.0$. That is, in the case of the form in which the catalytically active component x includes W, the amount of W in the catalytically active component x is more than 0 and 3.0 mol or less per 12 mol of Mo. When tungsten is contained, the specific surface area tends to increase and the catalytic activity tends to improve. However, if tungsten is contained in excess of 3.0 mol, the acrylic acid selectivity may decrease and the acrylic acid yield may decrease.

In the case of the form in which the catalytically active component x includes W, in the formula (1), c' for W (Wc') is preferably $0.1\leq c'\leq2.5$, more preferably $0.3\leq c'\leq2.0$, and further preferably $0.5\leq c'\leq1.5$. That is, the amount of W in the catalytically active component x is preferably 0.1 mol or more and 2.5 mol or less, more preferably 0.3 mol or more and 2.0 mol or less, and further preferably 0.5 mol or more and 1.5 mol or less, per 12 mol of Mo.

In view of maintaining high activity, the catalytically active component x is such that f and g are preferably 0 in the above formula (1). In addition, the C component in the composition of the above formula (1) can reduce the acrylic acid yield in some cases, and thus e is preferably 0. That is, the composition of the catalytically active component x (provided that oxygen in the oxidation state is omitted) when e, f, and g are 0 is represented by the following formula (2).

$$Mo_{12}Cu_aV_bA_cB_d \quad (2)$$

In the formula (2), the definitions of Mo, Cu, V, A, and B are the same as those in the formula (1), and the definitions of a, b, c, and d are the same as those in the formula (1). In the formula (2), preferably, A is at least one element selected from niobium and tungsten and B is at least one element selected from antimony and tellurium. In the formula (2), b is preferably $2\leq b\leq8$, more preferably $2\leq b\leq6$, and further preferably $3\leq b\leq5$; c is preferably $0.1\leq c\leq5$, more preferably $0.3\leq c\leq2$; and d is preferably $0.1\leq d\leq5$ and preferably $0.3\leq d\leq3$.

For example, in the case of the form in which the catalytically active component x includes Cu, the lower limit of a in the formula (2) is preferably $0<a$, more preferably $0.1\leq a$, and further preferably $0.2\leq a$. That is, the amount of Cu in the catalytically active component x is preferably more than 0 mol, more preferably 0.1 mol or more, and further preferably 0.2 mol or more, per 12 mol of Mo. In this case, the amount of Cu in the catalytically active component x is preferably less than 0.8 mol and more preferably 0.6 mol or less, and may be 0.5 mol or less, 0.4 mol or less, or 0.3 mol or less, per 12 mol of Mo.

In the case of the form in which the catalytically active component x includes W, in the formula (2), A includes tungsten (W). In this case, c for A (Ac) is $0<c\leq 12$ and c' for W (Wc') is $0<c'\leq 3.0$. That is, in the case of the form in which the catalytically active component x includes W, the amount of W in the catalytically active component x is more than 0 and 3.0 mol or less per 12 mol of Mo. When tungsten is contained, the specific surface area tends to increase and the catalytic activity tends to improve. However, if tungsten is contained in excess of 3.0 mol, the acrylic acid selectivity may decrease and the acrylic acid yield may decrease.

In the case of the form in which the catalytically active component x includes W, c' for W (Wc') in the formula (2) is preferably $0.1\leq c'\leq 2.5$, and more preferably $0.3\leq c' \leq 2.0$, and further preferably $0.5\leq c'\leq 1.5$. That is, the amount of W in the catalytically active component x is preferably 0.1 mol or more and 2.5 mol or less, more preferably 0.3 mol or more and 2.0 mol or less, and further preferably 0.5 mol or more and 1.5 mol or less, per 12 mol of Mo.

The catalytically active component x may be in a form including no Cu, that is, a form in which a is 0, in view of suppressing the combustion reaction of acrylic acid and, as a result, improving the yield of acrylic acid. In this case, the composition of the formula (2) in the form including no Cu is preferably a composition represented by the following formula (2-1), for example.

$$Mo_{12}V_bA_cB_d \quad (2\text{-}1)$$

In the formula (2-1), the definitions of Mo and V are the same as in the formula (1), A is at least one element selected from niobium and tungsten, B is at least one element selected from antimony and tellurium, and the definitions of b, c, and d are the same as those in the formulas (1) and (2).

In view of suppressing the combustion reaction of acrolein, the catalytically active component x may be in a form including Cu, and when Cu is included, a compound represented by, for example, the following formula (2-2) is preferable as a compound of the formula (2).

$$Mo_{12}Cu_aV_bA_cB_d \quad (2\text{-}2)$$

In the formula (2-2), the definitions of Mo, Cu, and V are the same as in the formula (1), A is at least one element selected from niobium and tungsten, B is at least one element selected from antimony and tellurium, $0<a\leq0.8$, and the definitions of b, c, and d are the same as those in the formulas (1) and (2).

In the formula (2-2), the lower limit of a is preferably $0.1\leq a$ and more preferably $0.2\leq a$. That is, the amount of Cu in the catalytically active component x is preferably 0.1 mol or more and more preferably 0.2 mol or more, per 12 mol of Mo. In this case, the amount of Cu in the catalytically active component x is preferably less than 0.8 mol and more preferably 0.6 mol or less, and may be 0.5 mol or less, 0.4 mol or less, or 0.3 mol or less, per 12 mol of Mo.

In the case of the form in which the catalytically active component x includes W, A in the formula (2-2) includes tungsten (W). In this case, c for A (Ac) is $0<c\leq12$ and c' for W (Wc') is $0<c'\leq3.0$. That is, in the case of the form in which the catalytically active component x includes W, the amount of W in the catalytically active component x is more than 0 and 3.0 mol or less per 12 mol of Mo. When tungsten is contained, the specific surface area tends to increase and the catalytic activity tends to improve. However, if tungsten is contained in excess of 3.0 mol, the acrylic acid selectivity may decrease and the acrylic acid yield may decrease.

In the case of the form in which the catalytically active component x includes W, c' for W (Wc') in the formula (2-2) is preferably $0.1\leq c'\leq2.5$, and more preferably $0.3\leq c'\leq2.0$, and further preferably $0.5\leq c'\leq1.5$. That is, the amount of W in the catalytically active component x is preferably 0.1 mol or more and 2.5 mol or less, more preferably 0.3 mol or more and 2.0 mol or less, and further preferably 0.5 mol or more and 1.5 mol or less, per 12 mol of Mo.

The specific surface area of the catalytically active component x is 15 $m^2/g$ to 40 $m^2/g$. If the specific surface area of the catalytically active component x is less than 15 $m^2/g$, the catalytic activity is insufficient and the yield of acrylic acid decreases. If the specific surface area of the catalytically active component x exceeds 40 $m^2/g$, the activity of the catalyst is too high and the acrylic acid generated is combusted, resulting in a decrease in the yield of acrylic acid. The specific surface area of the catalytically active component x is preferably 15 $m^2/g$ to 35 $m^2/g$, more preferably 15 $m^2/g$ to 30 $m^2/g$, further preferably 15 $m^2/g$ to 25 $m^2/g$, and more further preferably 16 $m^2/g$ to 25 $m^2/g$, more further preferably 17 $m^2/g$ to 25 $m^2/g$, and more further preferably 18 $m^2/g$ to 25 $m^2/g$. When the specific surface area of the catalytically active component x is within the above range, it is possible to suppress the combustion of acrylic acid while having sufficient catalytic activity, and it is possible to produce acrylic acid in high yield for a long period of time. The specific surface area of the catalytically active component x is calculated by the method described in Examples.

The average particle size of the catalytically active component x is not particularly limited, and is preferably 0.1 μm to 500 μm and more preferably 1 μm to 100 μm in view of excellent supportability. The average particle size of the catalytically active component x can be calculated as, for example, the median size (volume-based distribution) when the particle size distribution is measured using a particle size analyzer such as a laser diffraction/light scattering type particle size analyzer.

Here, the catalyst X may be formed by shaping the catalytically active component x alone, or may be a supported product obtained by supporting the catalytically active component x on a support such as alumina, silica, silica-alumina, titania, zirconia, magnesia, steatite, cordierite, silica-magnesia, silica-magnesia-alumina, silicon carbide, silicon nitride, zeolite, or stainless steel. In the case of a catalyst obtained by shaping the catalytically active component x alone, the catalyst X consists of the catalytically active component x. When the catalytically active component x is supported on a support, a supported product including the catalytically active component x and the support (on which the catalytically active component x is supported) serves as the catalyst X.

The shapes of the catalyst X and the support may be appropriately selected from shapes according to the purpose such as a pellet, a granule, a sphere, a ring, and a honeycomb and are not particularly limited.

The dimension of the catalyst X used in the present invention is not particularly limited, and the particle size of the catalyst X is preferably 1 mm to 12 mm and more preferably 3 mm to 10 mm. When the catalyst X is obtained by shaping the catalytically active component x, the catalyst X obtained by shaping the catalytically active component x having the above average particle size may have the above particle size of the catalyst X. When the catalyst X is obtained by supporting the catalytically active component x on a support, the catalyst X having the target particle size (specifically, a catalyst X where the catalytically active component x is supported) can be obtained by using a support having a particle size smaller than a target particle size (that is, the above particle size of the catalyst X) by 0.5 to 1.0 mm and regulating the supporting time. Here, the particle size of the catalyst X refers to the diameter thereof in the case of a spherical catalyst, and to the diameter of a circumscribed sphere of the catalyst in the case of a different shape. When the average particle size of the catalyst X is within the above range, the catalyst X can be easily packed in the reaction tube and the pressure drop of the catalyst layer can be reduced to achieve energy saving such as reduction of the electric power cost of a blower. The average particle size of the catalyst X can be measured by measuring the particle sizes of 100 arbitrarily sampled catalysts X using calipers and calculating the average value.

When the catalytically active component x is supported on a support, the supporting rate of the catalytically active component x in the catalyst X, that is, the proportion of the mass of the catalytically active component x to the mass of the catalyst X (the total mass of the catalytically active component x and the support) is preferably 5 to 50% by mass, more preferably 10 to 40% by mass, and further preferably 15 to 30% by mass.

In the catalyst layer including the catalyst X, the shape of the catalyst X to be packed in the catalyst layer may be the same or different, and it is preferable to pack the catalyst X having the same shape.

For the method for producing the catalyst X, the catalyst X can be prepared by a method generally used for the preparation of this kind of catalyst.

The catalyst X obtained by shaping the catalytically active component x can be obtained, for example by a production method comprising a step of, first, mixing each starting material including each metal element for the catalytically active component x into water or the like and dissolving or dispersing the same to form a solution or a dispersion, mixing the solution(s) and/or the dispersion(s) to form a slurry, and reacting the slurry under the conditions of temperature and pressure described later; a step of drying the resulting slurry and as necessary pulverizing the same to obtain a precursor of the catalytically active component x in the form of a powder; a step of calcining this precursor of the catalytically active component x to obtain the catalytically active component x; and a step of shaping the catalytically active component x. The catalyst X can also be obtained by a production method comprising, after obtaining the precursor of the catalytically active component x in the form of a powder, a step of shaping the precursor of the catalytically active component x in the form of a powder; and a step of calcining this shaped precursor.

The catalyst X obtained by supporting the catalytically active component x on a support can be obtained, for example by a production method comprising a step of, first, mixing each starting material including each metal element for the catalytically active component x into water or the like and dissolving or dispersing the same to form a solution or a dispersion, mixing the solution(s) and/or the dispersion(s) to form a slurry, and reacting the slurry under the conditions of temperature and pressure described later; a step of drying the slurry and as necessary pulverizing the same to obtain a precursor of the catalytically active component x in the form of a powder; a step of contacting this precursor of the catalytically active component x with a support to form a supported product where the precursor of the catalytically active component x is supported and then calcining the supported product to obtain a supported product where the catalytically active component x is supported (catalyst X). The catalyst X can also be obtained by a production method including a step of calcining the precursor of the catalytically active component x in the form of a powder to obtain a catalytically active component x in the form of a powder; a step of contacting this catalytically active component x with a support to obtain a supported product where the catalytically active component x is supported (catalyst X); and as necessary a step of calcining the supported product again.

The starting material used for preparing the catalytically active component x is not particularly limited, and generally used ammonium salts, organic ammonium salts, nitrates, carbonates, oxalates, organic carboxylates, sulfates, hydroxides, and oxides of metal elements, metal species, and the like are used. A compound including a plurality of metal elements may be used.

For the catalytically active component of the present invention, a catalytically active component having a desired specific surface area can be obtained by adjusting the calcination temperature, the calcination time, the calcination atmosphere, the slurry preparation and its reaction method, and the like. For a catalyst containing niobium or tantalum, the calcination temperature is 250° C. to 750° C., preferably 280° C. to 700° C., and further preferably 300° C. to 660° C., and the calcination time is preferably 1 hour to 20 hours, more preferably 1 hour to 12 hours, and further preferably 1 hour to 8 hours. For a catalyst containing no niobium or tantalum, the calcination temperature is 250° C. to 600° C., preferably 300° C. to 550° C., and further preferably 350° C. to 450° C., and the calcination time is preferably 1 hour to 20 hours, more preferably 1 hour to 10 hours, and further preferably 1 hour to 5 hours. With a higher calcination temperature and a longer the calcination time within the above ranges, the catalytically active component with a smaller specific surface area is obtained. The calcination atmosphere can be appropriately selected from an air atmosphere, an inert gas atmosphere, a water vapor atmosphere, an atmosphere including a reducing gas such as ammonia and hydrogen, an atmosphere of a mixed gas thereof, or the like. The relationship between the calcination atmosphere and the specific surface area changes depending on the composition of the catalytically active component, and thus the calcination atmosphere may be appropriately selected according to the composition of the catalytically active component.

For methods for slurry preparation and reaction, the slurry preparation and reaction may be carried out under atmospheric pressure, and for an acrolein oxidation catalyst, it is preferable to carry out the slurry preparation and reaction under high temperature and high pressure conditions using an autoclave because the specific surface area of the catalytically active component generally become higher. The temperature at which the slurry preparation and reaction are carried out under atmospheric pressure is 60° C. to 120° C. and preferably 70° C. to 100° C. At this time, the higher the temperature, the higher the solubility of the material in the slurry; however, if the temperature is too high, the concentration of the slurry increases because of the evaporation of water and the solubility of the material decreases. Reflux may be carried out to suppress an increase in slurry concentration during slurry preparation. When the slurry preparation and reaction are carried out in an autoclave, the temperature is 120° C. to 300° C. and preferably 150° C. to 250° C., and the pressure is 0.5 MPa to 10 MPa and preferably 1 MPa to 5 MPa. If the temperature and the pressure are high, the reaction proceeds quickly to shorten the preparation time, but on the other hand, expensive high pressure equipment is required.

The method for detecting the catalyst X (catalytically active component x) of the present invention is not particularly limited, and examples thereof include the following method. When the catalytically active component x is supported on a support, 20 g of the catalyst X is placed in a stainless steel cylindrical container having an inner diameter of 70 mm and a height of 140 mm. In order to shake off the catalytically active component x on the surface of the catalyst X, the container including the catalyst X is set in a shaker and the catalyst X is shaken at a rate of 100 times to 200 times/minute in the long side direction of the stainless steel cylindrical container with an amplitude of 80 mm to 300 mm for 5 minutes. Of the powder shaken off, a powder of 100 μm or less is sieved and XRF analysis is carried out to identify an element and calculate the content thereof. In addition, the specific surface area of the powder of 100 μm or less is measured using a BET specific surface area measuring apparatus. If the element contained in the powder, the content thereof, and the specific surface area of the powder are the same as those of the catalytically active component x of the present invention, the catalytically active component is regarded as the catalytically active component x.

Next, catalyst layers other than the catalyst layer including the catalyst X (hereinafter, referred to as other catalyst layers) will be described.

In the method for producing acrylic acid according to the present invention, the number of catalyst layers other than the catalyst layer including the catalyst X (hereinafter, referred to as other catalyst layers) is preferably large in view of suppressing the temperature rise in the catalyst layers, but if the catalyst layer including the catalyst X and other catalyst layers are present, the target advantageous effects of the present invention can be sufficiently obtained. Accordingly, the number of all catalyst layers (total number of layers of the catalyst layer including the catalyst X and other catalyst layers) may be 2 or more layers, and is preferably 3 to 5 layers. The ratio (layer length ratio) between the length of the catalyst layer including the catalyst X and the length of other catalyst layers, and the layer length ratio of each catalyst layer in the other catalyst layers depend on the target reaction conditions and the compositions, shapes, and sizes of the catalyst layer including catalyst X and the other catalyst layers. Thus these ratios cannot be unconditionally specified and may be appropriately selected so as to obtain the optimum activity and selectivity as a whole.

The catalyst to be packed in each catalyst layer other than the catalyst layer including the catalyst X (hereinafter, referred to as a catalyst other than the catalyst X) is not particularly limited as long as it converts acrolein into acrylic acid, and a known catalyst generally used for the vapor phase catalytic oxidation reaction can be used.

The catalyst other than the catalyst X may be a shaped catalyst in which the catalytically active component has a certain shape, a supported catalyst where the catalytically active component is supported on an arbitrary inert support having a certain shape, or a combination of the shaped catalyst and the supported catalyst. In the other catalyst layers, the shape of the catalyst to be packed in each catalyst layer may be the same or different, and usually, a catalyst and/or a supported catalyst having the same shape is preferably packed in the same catalyst layer.

The shape of the catalyst other than the catalyst X may be appropriately selected from shapes according to the purpose such as a pellet, a granule, a sphere, a ring, and a honeycomb and is not particularly limited.

When a catalyst other than the catalyst X is a supported catalyst, the supporting rate of the catalyst to be packed in each catalyst layer may be the same or different. In addition, the support is not particularly limited, and a support that can usually be used for producing a catalyst for vapor phase catalytic oxidation can be used. Specific examples of the support that can be used include alumina, silica, silica-alumina, titania, zirconia, magnesia, steatite, cordierite, silica-magnesia, silica-magnesia-alumina, silicon carbide, silicon nitride, zeolite, and stainless steel. The supporting rate of the catalyst is not particularly limited, and is preferably 10 to 100% by mass.

It is possible to pack the catalyst X in a reaction tube of the fixed bed reactor before starting the vapor phase catalytic oxidation reaction of acrolein using a fixed bed reactor, that is, before supplying a acrolein-containing gas to a fixed bed reactor. It is also possible to stop the reaction temporarily after the vapor phase catalytic oxidation reaction is continued for a certain period of time, partially replace the catalyst in the outlet portion of the reaction tube of the fixed bed reactor with the catalyst X, and then supply an acrolein-containing gas to restart the reaction. It is also possible to stop the reaction temporarily, additionally pack the catalyst X in the last stage of the catalyst layer of the reaction tube of the fixed bed reactor, and then restart the reaction.

Thus, according to the present invention, there is also provided a method for packing a catalyst in a reaction tube of a fixed bed reactor. Specifically, provided is a method for packing a catalyst used for producing acrylic acid, and the method is for packing a catalyst in a reaction tube of a fixed bed reactor used for producing acrylic acid by vapor phase catalytic oxidation of acrolein. In this method, the reaction tube is packed with two or more catalysts having different activities in such a way that two or more catalyst layers are formed in a tube axis direction of the reaction tube; a catalyst X having the highest activity among the catalysts contained in all the catalyst layers is packed in such a way as to be placed in the whole or a part of a section up to 30% of the length of all the catalyst layers from the rearmost portion on the gas outlet side toward the gas inlet side of all the catalyst layers; a catalytically active component x in the catalyst X has Mo, V, and optionally Cu, and when Cu is included, the amount thereof is 0.8 mol or less per 12 mol of Mo; and the specific surface area of the catalytically active component x is 15 $m^2/g$ to 40 $m^2/g$. The catalyst X can be prepared by the method described herein, and the specific surface area and the activity of the catalyst can be measured by the methods described herein and the methods described in Examples described later.

In the present invention, a gas containing acrolein is used as a reactant gas. Examples of the acrolein-containing gas include a gas of acrolein alone, a mixed gas including acrolein and at least one of molecular oxygen and an inert gas, a mixed gas containing acrolein obtained by vapor phase catalytic oxidation of propylene, and a mixed gas containing acrolein obtained by dehydration reaction of glycerin. In addition, air or oxygen or water vapor, an inert gas such as nitrogen, or another gas can be added to the above acrolein-containing gas as necessary, before use.

The reaction conditions in the production of acrylic acid of the present invention are not particularly limited, and any of the conditions used for this type of reaction can be used. For example, as the acrolein-containing gas, a mixed gas consisting of 7 to 13% by volume of acrolein, 2 to 20% by volume of molecular oxygen, 2 to 40% by volume of water vapor, and the balance of an inert gas such as nitrogen may be supplied from the gas inlet side of the reaction tube of the fixed bed reactor in a reaction temperature range of 200 to 400° C. under a pressure of 0.1 to 1.0 MPa at a space velocity of 1000 to 10000 $h^{-1}$ (STP) and contacted with all the catalyst layers in the reaction tube to cause reaction.

In the method for producing acrylic acid according to the present invention, the reaction temperature is preferably 220 to 300° C. and more preferably 250 to 285° C. At such a reaction temperature, the life of the catalyst can be extended and a high acrylic acid yield can be developed, according to the method for producing acrylic acid according to the present invention in which a catalyst containing no or a small amount of Cu is placed in the latter half of the reaction tube. In the method for producing acrylic acid according to the present invention, the reaction temperature is preferably 220 to 300° C. and more preferably 250 to 285° C. even after 8000 hours have passed from the start of the reaction (start of flow of an acrolein-containing gas), as shown in Examples described later. That is, according to the present invention, the occurrence of an abnormal temperature rise in the catalyst layer is suppressed, and the life of the catalyst is extended.

In the present invention, the reaction temperature means the temperature of a heat medium, and specifically, as in Examples described later, can be determined by measuring the temperature of the heat medium in the vicinity of a middle portion of the layer length of all the catalyst layers during the reaction.

According to the method for producing acrylic acid according to the present invention, the life of the catalyst can be extended and a high acrylic acid yield can be developed even under a high load condition, as described above. Specifically, for example, even when the space time yield (STY [Standard Time Yield]: the amount of acrylic acid produced by a catalyst having a unit volume in a unit time) is 400 $kg/(m^3 \cdot h^{-1})$ (STP) or more, it is possible to extend the life of the catalyst and increase the yield of acrylic acid. In the method for producing acrylic acid according to the present invention, even when the load (the amount of acrolein acting on a catalyst having a unit volume in a unit time) is 450 $kg/(m^3 \cdot h^{-1})$ (STP) or more, it is possible to extend the life of the catalyst and increase the yield of acrylic acid.

The vapor phase catalytic oxidation reaction in the present invention may be carried out by a usual one-pass method or recycling method, and can be carried out under conditions generally used for this kind of reaction.

EXAMPLES

The present invention will be described in more detail using the following Examples and Comparative Examples. However, the technical scope of the present invention is not limited only to the following Examples. Unless otherwise specified, "%" and "parts" mean "% by mass" and "parts by mass," respectively. In the following Examples, the operations were carried out under the condition of room temperature (20 to 25° C.), unless otherwise specified.

[Catalyst Preparation Method]

1. Preparation of Catalyst (1)

While 10000 g of pure water was heated and stirred, 1000 g of ammonium paramolybdate tetrahydrate, 303 g of ammonium metavanadate, and 153 g of ammonium paratungstate tetrahydrate were dissolved therein. Separately, while 400 g of pure water was heated and mixed, 171 g of copper nitrate trihydrate was dissolved therein. The two aqueous solutions obtained were mixed, and 35 g of antimony trioxide and 424 g of aluminum oxide were further added to obtain a starting material mixture. The starting material mixture obtained was dried using a spray dryer, and then the dried product obtained was pulverized and sieved to 100 μm or less to obtain a precursor of a catalytically active component. 3960 g of a spherical silica-alumina support having an average diameter of 8 mm was fed into a pan-type tumbling granulator. Subsequently the precursor of the catalytically active component was gradually fed while spraying pure water as a binder with the rotary pan rotated to thereby support the precursor on the support, and then the resultant was dried using hot air at about 90° C. to obtain a supported product where the precursor of the catalytically active component was supported. The supported product obtained was calcined at 400° C. for 6 hours in an air atmosphere to obtain a catalyst (1). The supporting rate was 30% by mass, and the specific surface area of the catalytically active component was 7.7 $m^2/g$. The metal element composition of the catalytically active component with omission of oxygen was as follows.

$Mo_{12}Cu_{1.5}V_{5.5}W_{1.2}Sb_{0.5}Al_{17.6}$ Catalyst (1)

2. Preparation of Catalysts (2) and (3)

A precursor of a catalytically active component for a catalyst (2) and a catalyst (3) was obtained in the same manner as in the method for preparing the catalyst (1) except that aluminum oxide was not used. Next, a supported product for the catalyst (2) having a supporting rate of 30% by mass and a supported product for the catalyst (3) having a supporting rate of 40% by mass were obtained in the same manner as in the method for preparing the catalyst (1) except for using a spherical silica-alumina support having an average diameter of 5 mm as the support and adjusting the amount of the precursor of the catalytically active component to be fed into the pan-type tumbling granulator. These supported products were further calcined under the same conditions to obtain the catalyst (2) (supporting rate of 30%) and the catalyst (3) (supporting rate of 40%). The specific surface area of the catalytically active component was 9.9 $m^2/g$. The metal element composition of the catalytically active component with omission of oxygen was as follows.

$Mo_{12}Cu_{1.5}V_{5.5}W_{1.2}Sb_{0.5}$ Catalyst (2) and catalyst (3)

3. Preparation of Catalyst (4)

While 3500 g of pure water was heated and stirred, 576 g of molybdenum(VI) oxide, 109 g of vanadium(V) oxide, 58 g of antimony trioxide, and 260 g of ammonium niobium oxalate (containing 24.8% by mass as $Nb_2O_5$) were added thereto and the resultant was heated and stirred at 175° C. for 24 hours in a closed autoclave to obtain a starting material mixture. The starting material mixture obtained was filtered to separate the precipitate, and the precipitate was dried at 80° C. for 15 hours in a box-type drying oven. The dried product was pulverized and sieved to 100 μm or less to obtain a precursor of a catalytically active component. 2700 g of a spherical silica-alumina support having an average diameter of 5 mm was fed into a pan-type tumbling granulator. Subsequently the precursor of the catalytically active component was gradually fed while spraying pure water as a binder with the rotary pan rotated to thereby support the precursor on the support, and then the resultant was dried using hot air at about 90° C. to obtain a supported product. The supported product obtained was calcined at 600° C. for 6 hours in a nitrogen atmosphere to obtain a catalyst (4). The supporting rate was 23% by mass, and the specific surface area of the catalytically active component was 23.7 $m^2/g$. The metal element composition of the catalytically active component with omission of oxygen was as follows.

$Mo_{12}V_{3.6}Nb_{1.5}Sb_{1.2}$ Catalyst (4)

4. Preparation of Catalyst (5)

A catalyst (5) was obtained in the same manner as in the method for preparing the catalyst (4) except that calcining was carried out at 640° C. The specific surface area of the catalytically active component was 11.3 $m^2/g$. The metal element composition of the catalytically active component of the catalyst (5) is the same as that of the catalyst (4).

5. Preparation of Catalyst (6)

While 3500 g of pure water was heated and stirred, 576 g of molybdenum(VI) oxide, 109 g of vanadium(V) oxide, 58 g of antimony trioxide, 8.0 g of copper(II) oxide, and 260 g of ammonium niobium oxalate (containing 24.8% by mass as $Nb_2O_5$) were added thereto and the resultant was heated and stirred at 175° C. for 24 hours in a closed autoclave to obtain a starting material mixture. The starting material mixture obtained was filtered to separate the precipitate, and the precipitate was dried at 80° C. for 15 hours in a box-type drying oven. The dried product was pulverized and sieved to 100 μm or less to obtain a precursor of a catalytically active component. 2700 g of a spherical silica-alumina support having an average diameter of 5 mm was fed into a pan-type tumbling granulator. Subsequently the precursor of the catalytically active component was gradually fed while spraying pure water as a binder with the rotary pan rotated support the precursor on the support, and then the resultant was dried using hot air at about 90° C. to obtain a supported product. The supported product obtained was calcined at 590° C. for 6 hours in a nitrogen atmosphere to obtain a catalyst (6). The supporting rate was 23% by mass, and the specific surface area of the catalytically active component was 27.7 $m^2/g$. The metal element composition of the catalytically active component with omission of oxygen was as follows.

$Mo_{12}Cu_{0.3}V_{3.6}Nb_{1.5}Sb_{1.2}$ Catalyst (6)

6. Preparation of Catalyst (7)

While 10000 g of pure water was heated and stirred, 2180 g of ammonium paramolybdate tetrahydrate, 344 g of ammonium metavanadate, 466 g of antimony trioxide, and 114 g of 30% by mass hydrogen peroxide aqueous solution were added thereto to obtain a molybdenum-containing mixture (mixture A).

Separately, while 4000 g of pure water was heated and stirred, 493 g of oxalic acid, anhydrous and 478 g of niobic acid (containing 37.8% by mass as $Nb_2O_5$) were added thereto to obtain a niobium-containing mixture (mixture B). Mixture A and mixture B were mixed to obtain a starting material mixture. The starting material mixture was dried using a spray drying oven, and then the dried product obtained was pulverized and sieved to 100 μm or less to obtain a precursor of a catalytically active component. 9000 g of a spherical silica-alumina support having an average diameter of 5 mm was fed into a pan-type tumbling granulator. Subsequently the precursor of the catalytically active component was gradually fed while spraying pure water as a binder with the rotary pan rotated to thereby support the precursor on the support, and then the resultant was dried using hot air at about 90° C. to obtain a supported product. The supported product obtained was calcined at 600° C. for 6 hours in a nitrogen atmosphere to obtain a catalyst (7). The supporting rate was 23% by mass, and the specific surface area was 18.9 $m^2/g$. The metal element composition of the catalytically active component with omission of oxygen was as follows.

$Mo_{12}V_{2.9}Nb_{1.3}Sb_{3.1}$ Catalyst (7)

7. Preparation of Catalyst (8)

While 3500 g of pure water was heated and stirred, 576 g of molybdenum(VI) oxide, 109 g of vanadium(V) oxide, 106 g of tellurium dioxide, and 260 g of ammonium niobium oxalate (containing 24.8% by mass as $Nb_2O_5$) were added thereto and the resultant was heated and stirred at 175° C. for 24 hours in a closed autoclave to obtain a starting material mixture. The starting material mixture obtained was filtered to separate the precipitate, and the precipitate was dried at 80° C. for 15 hours in a box-type drying oven. The dried product was pulverized and sieved to 100 pin or less to obtain a precursor of a catalytically active component. 2850 g of a spherical silica-alumina support having an average diameter of 5 mm was fed into a pan-type tumbling granulator. Subsequently the precursor of the catalytically active component was gradually fed while spraying pure water as a binder with the rotary pan rotated to thereby support the precursor on the support, and then the resultant was dried using hot air at about 90° C. to obtain a supported product. The supported product obtained was calcined at 600° C. for 6 hours in a nitrogen atmosphere to obtain a catalyst (8). The supporting rate was 23% by mass, and the specific surface area of the catalytically active component was 19.5 $m^2$/g. The metal element composition of the catalytically active component with omission of oxygen was as follows.

$Mo_{12}V_{3.6}Nb_{1.5}Te_{2.0}$ Catalyst (8)

8. Preparation of Catalyst (9)

While 10000 g of pure water was heated and stirred at 80° C., 412 g of ammonium paramolybdate tetrahydrate and 73 g of ammonium metavanadate were dissolved therein. This solution was cooled to 50° C., then 307 g of an aqueous dispersion containing 42 g of a metal tellurium particle obtained by reducing tellurium dioxide using hydrazine was added, and 128 g of 10% ammonia aqueous solution was further added dropwise to obtain mixture C. Separately, while 1910 g of pure water was heated and stirred, 186 g of oxalic acid, 130 g of niobic acid (containing 37.8% by mass as $Nb_2O_5$), and 31 g of 30% by mass hydrogen peroxide aqueous solution were added thereto to obtain mixture D. Mixture D was added to mixture C, the resulting mixture was stirred for 10 minutes, then 107 g of ammonium nitrate was added, and the resulting mixture was stirred for 15 hours. The starting material mixture obtained was dried using a spray drying oven, and then the dried product (a precursor of a catalytically active component) was calcined at 320° C. for 1.5 hours in an air atmosphere. The solid particle thus obtained was further calcined at 600° C. for 2.0 hours under nitrogen flow. The calcined product obtained was pulverized and sieved to 100 μm or less to obtain a catalytically active component. 1650 g of a spherical silica-alumina support having an average diameter of 5 mm was fed into a pan-type tumbling granulator. Subsequently the catalytically active component was gradually fed while spraying pure water as a binder with the rotary pan rotated to thereby support the catalytically active component on the support, and then the resultant was dried using hot air at about 90° C. to obtain a catalyst (9). The supporting rate was 23% by mass, and the specific surface area of the catalytically active component was 15.1 $m^2$/g. The metal element composition of the catalytically active component with omission of oxygen was as follows.

$Mo_{12}V_{3.2}Nb_{1.9}Te_{1.7}$ Catalyst (9)

9. Preparation of Catalyst (10)

While 3500 g of pure water was heated and stirred, 576 g of molybdenum(VI) oxide, 127 g of vanadium(V) oxide, 43 g of ammonium metatungstate (containing 90.8% by mass as $WO_3$), 49 g of antimony trioxide, 13 g of copper(II) oxide, and 176 g of oxalic acid dihydrate were added thereto and the resultant was heated and stirred at 180° C. for 24 hours in a closed autoclave to obtain a starting material mixture. The starting material mixture obtained was filtered to separate the precipitate, and the precipitate was dried at 80° C. for 15 hours in a box-type drying oven. The dried product was pulverized and sieved to 100 pin or less to obtain a precursor of a catalytically active component. 2700 g of a spherical silica-alumina support having an average diameter of 5 mm was fed into a pan-type tumbling granulator. Subsequently the precursor of the catalytically active component was gradually fed while spraying pure water as a binder with the rotary pan rotated to thereby support the precursor on the support, and then the resultant was dried using hot air at about 90° C. to obtain a supported product. The supported product obtained was calcined at 400° C. for 2 hours in an air atmosphere to obtain a catalyst (10). The supporting rate was 23% by mass, and the specific surface area of the catalytically active component was 17.6 $m^2$/g. The metal element composition of the catalytically active component with omission of oxygen was as follows.

$Mo_{12}Cu_{0.5}V_{4.2}W_{0.5}Sb_{1.0}$ Catalyst (10)

10. Preparation of Catalyst (11)

A catalyst (11) was obtained in the same manner as in the method for preparing the catalyst (10) except that 16 g of copper(II) oxide was used. The specific surface area of the catalytically active component was 17.5 $m^2$/g. The metal element composition of the catalytically active component with omission of oxygen was as follows.

$Mo_{12}Cu_{0.6}V_{4.2}W_{0.5}Sb_{1.0}$ Catalyst (11)

11. Preparation of Catalyst (12)

A catalyst (12) was obtained in the same manner as in the method for preparing the catalyst (10) except that 21 g of copper(II) oxide was used. The specific surface area of the catalytically active component was 17.3 $m^2$/g. The metal element composition of the catalytically active component with omission of oxygen was as follows.

$Mo_{12}Cu_{0.8}V_{4.2}W_{0.5}Sb_{1.0}$ Catalyst (12)

12. Preparation of Catalyst (13)

A catalyst (13) was obtained in the same manner as in the method for preparing the catalyst (10) except that 26 g of copper(II) oxide was used. The specific surface area of the catalytically active component was 17.2 $m^2$/g. The metal element composition of the catalytically active component with omission of oxygen was as follows.

$Mo_{12}Cu_{1.0}V_{4.2}W_{0.5}Sb_{1.0}$ Catalyst (13)

13. Preparation of Catalyst (14)

A catalyst (14) was obtained in the same manner as in the method for preparing the catalyst (10) except that calcining was carried out at 420° C. The specific surface area of the catalytically active component was 12.9 $m^2$/g. The metal element composition of the catalytically active component of the catalyst (14) is the same as that of the catalyst (10).

14. Preparation of Catalyst (15)

While 6000 g of pure water was heated and stirred, 210 g of ammonium paramolybdate tetrahydrate, 80 g of vanadium(IV) oxide sulfate, and 20 g of ammonium metatungstate (containing 90.8% by mass as $WO_3$) were added thereto and the resultant was heated and stirred at 185° C. for 50 hours in a closed autoclave to obtain a starting material mixture. The starting material mixture obtained was filtered to separate the precipitate, and the precipitate dried at 120° C. for 15 hours in a box-type drying oven. The dried product was pulverized and sieved to 100 μm or less to obtain a precursor of a catalytically active component. 165 g of a spherical silica-alumina support having an average diameter of 5 mm was fed into a pan-type tumbling granulator. Subsequently 50 g of the precursor of the catalytically active component was gradually fed while spraying pure water as a binder with the rotary pan rotated to thereby support the precursor on the support, and then the resultant was dried using hot air at about 90° C. to obtain a supported product. The supported product obtained was calcined at 430° C. for 2 hours in a nitrogen atmosphere to obtain a catalyst (15). The supporting rate was 23% by mass, and the specific surface area of the catalytically active component was 37.5 $m^2/g$. The metal element composition of the catalytically active component with omission of oxygen was as follows. In the preparation of the catalyst (15), the yield of the precipitate obtained from the starting material mixture is low, and thus the catalyst (15) has a metal element composition different from the composition of the starting materials added.

$Mo_{12}V_{4.5}W_{0.6}$ Catalyst (15)

15. Preparation of Catalyst (16)

While 6000 g of pure water was heated and stirred, 175 g of molybdenum(VI) oxide, 16 g of a monomethylamine aqueous solution (40% by mass), 80 g of vanadium(IV) oxide sulfate, 21 g of ammonium metatungstate (containing 90.8% by mass as $WO_3$), and 4.8 g of copper sulfate pentahydrate were added thereto and the resultant was heated and stirred at 185° C. for 50 hours in a closed autoclave to obtain a starting material mixture. The starting material mixture obtained was filtered to separate the precipitate, and the precipitate was dried at 120° C. for 15 hours in a box-type drying oven. The dried product was pulverized and sieved to 100 μm or less to obtain a precursor of a catalytically active component. 165 g of a spherical silica-alumina support having an average diameter of 5 mm was fed into a pan-type tumbling granulator. Subsequently 50 g of the precursor of the catalytically active component was gradually fed while spraying pure water as a binder with the rotary pan rotated to thereby support the precursor on the support, and then the resultant was dried using hot air at about 90° C. to obtain a supported product. The supported product obtained was calcined at 400° C. for 2 hours in an air atmosphere to obtain a catalyst (16). The supporting rate was 23% by mass, and the specific surface area of the catalytically active component was 44.8 $m^2/g$. The metal element composition of the catalytically active component with omission of oxygen was as follows. In the preparation of the catalyst (16), the yield of the precipitate obtained from the starting material mixture is low, and thus the catalyst (16) has a metal element composition different from the composition of the starting materials added.

$Mo_{12}Cu_{0.3}V_{4.5}W_{0.6}$ Catalyst (16)

16. Preparation of Catalyst (17)

The catalyst (17) was prepared according to Production Example 12 (Production of Catalyst (12)) of JPA 2003-89671.

While 10000 g of pure water was heated and stirred, 1350 g of ammonium paramolybdate tetrahydrate, 410 g of ammonium metavanadate, and 207 g of ammonium paratungstate tetrahydrate were dissolved therein. Separately, while 500 g of pure water was heated and stirred, 506 g of copper nitrate trihydrate and 154 g of iron(III) nitrate nonahydrate were dissolved therein. The two aqueous solutions obtained were mixed, and 46 g of antimony trioxide was further added to obtain a starting material mixture. This mixture was evaporated to dryness while being heated and stirred, and the resultant was then dried at 120° C. for 5 hours in a drying oven. The dried product was pulverized and sieved to 100 μm or less to obtain a precursor of a catalytically active component. 5500 g of a spherical silica-alumina support having an average diameter of 5 mm was fed into a pan-type tumbling granulator. Subsequently the precursor of the catalytically active component was gradually fed while spraying pure water as a binder with the rotary pan rotated to thereby support the precursor on the support, and then the resultant was dried using hot air at about 90° C. to obtain a supported product. The supported product obtained was calcined at 400° C. for 6 hours in an air atmosphere to obtain a catalyst (17). The supporting rate was 25% by mass, and the specific surface area of the catalytically active component was 9.6 $m^2/g$. The metal element composition of the catalytically active component with omission of oxygen was as follows.

$Mo_{12}Cu_{3.3}V_{5.5}W_{1.2}Sb_{0.5}Fe_{0.6}$ Catalyst (17)

17. Preparation of Catalyst (18)

The catalyst (18) was prepared according to Production Example 13 (Production of Catalyst (13)) of JPA 2003-89671.

While 10000 g of pure water was heated and stirred, 1350 g of ammonium paramolybdate tetrahydrate, 410 g of ammonium metavanadate, and 207 g of ammonium paratungstate tetrahydrate were dissolved therein. Separately, while 500 g of pure water was heated and stirred, 123 g of copper nitrate trihydrate and 77 g of iron(III) nitrate nonahydrate were dissolved therein. The two aqueous solutions obtained were mixed, and 46 g of antimony trioxide was further added to obtain a starting material mixture. This mixture was evaporated to dryness while being heated and stirred, and the resultant was then dried at 120° C. for 5 hours in a drying oven. The dried product was pulverized and sieved to 100 μm or less to obtain a precursor of a catalytically active component. 5100 g of a spherical silica-alumina support having an average diameter of 5 mm was fed into a pan-type tumbling granulator. Subsequently the precursor of the catalytically active component was gradually fed while spraying pure water as a binder with the rotary pan rotated to thereby support the precursor on the support, and then the resultant was dried using hot air at about 90° C. to obtain a supported product. The supported product obtained was calcined at 400° C. for 6 hours in an air atmosphere to obtain a catalyst (18). The supporting rate was 25% by mass, and the specific surface area of the catalytically active component was 10.2 $m^2/g$. The metal element composition of the catalytically active component with omission of oxygen was as follows.

$Mo_{12}Cu_{0.8}V_{5.5}W_{1.2}Sb_{0.5}Fe_{0.3}$ Catalyst (18)

18. Preparation of Catalysts (19) and (20)

The catalysts (19) and (20) were prepared according to Example 1 of JPA H07-10802.

While 10000 g of pure water was heated and stirred, 1400 g of ammonium paramolybdate tetrahydrate, 232 g of ammonium metavanadate, and 54 g of monoethanolamine were dissolved therein. Separately, while 500 g of pure water was heated and stirred, 495 g of copper sulfate pentahydrate and 186 g of cobalt sulfate heptahydrate were dissolved therein. The two aqueous solutions obtained were mixed, and 199 g of a 20% by mass silica sol was further added to obtain a starting material mixture. This mixture was concentrated while being heated and stirred, and then the resultant in the form of a slurry was taken out and dried under air flow at 200° C. for 14 hours using a drying oven. Subsequently, the dried product was heat-treated at 250° C. for 3 hours. The solid obtained was pulverized and sieved to 100 μm or less to obtain a precursor of a catalytically active component. A spherical silica-alumina support having an average diameter of 5 mm was fed into a pan-type tumbling granulator. Subsequently the precursor of the catalytically active component was gradually fed while spraying pure water as a binder with the rotary pan rotated to thereby support the precursor on the support, and then the resultant was dried using hot air at about 90° C. to obtain a supported product. The supported product obtained was packed in a container (250 mm×170 mm×50 mm rectangular parallelepiped with a lid with a hole of 3 mmφ) at a rate of 1.3 kg per container. This was placed in a calcining furnace and calcined by heating to 380° C. and holding for 3 hours. The calcined product was temporarily taken out of the container, transferred to an open type container, and further calcined at 300° C. for 6 hours under air flow to obtain a catalyst. Here, the amount of the precursor of the catalytically active component to be fed when supporting the same using a pan-type tumbling granulator was adjusted so as to obtain a catalyst (19) having a supporting rate of 23% by mass and a catalyst (20) having a supporting rate of 31% by mass. The specific surface area of the catalytically active component was 8.1 $m^2/g$. The metal element composition of the catalytically active component with omission of oxygen was as follows.

$Mo_{12}Cu_{3.0}V_{3.0}Co_{1.0}Si_{1.0}$ Catalyst (19) and catalyst (20)

For the catalysts (1) to (20) obtained, the metal element composition, the Cu content, and the specific surface area of the catalytically active component, the average diameter of the support used and the supporting rate of the catalytically active component, and the catalytic activity are shown in Table 1. In Table 1, "Amount of Cu [vs. 12Mo]" means the amount of Cu per 12 mol of Mo.

Here, the supporting rate of the catalytically active component, the specific surface area of the catalytically active component, and the catalytic activity were measured and calculated according to the following definitions and methods. In addition, as a result of measurement using a laser diffraction/light scattering particle size analyzer (product name: LA-920, manufactured by HORIBA, Ltd.), the average particle sizes (median sizes of volume-based distributions) of the catalytically active components (1) to (20) were 1 to 50 μm.

[Supporting Rate]

The supporting rate of a catalyst is defined by the following expression:

Supporting rate (%)=(Catalyst weight−support weight)/Catalyst weight×100

[Specific Surface Area]

The specific surface area refers to the surface area per unit weight ($m^2/g$), and the specific surface area of the catalytically active component was measured by using a BET specific surface area analyzer and adsorbing nitrogen on 1 g of a powder at −198° C. until the adsorption equilibrium pressure/saturated vapor pressure reached 0.3, followed by determination from the amount of nitrogen adsorbed using the single point BET method.

[Evaluation of Catalytic Activity]

The activity of the catalysts (1) to (20) obtained was evaluated by carrying out vapor phase catalytic oxidation reaction of acrolein using each of the catalysts (1) to (20) alone (in a single layer) according to the following methods and calculating the acrolein conversion rate at that time.

<Vapor Phase Catalytic Oxidation Reaction of Acrolein in Single Layer>

The catalyst (1) was packed in one end of a stainless steel U-shaped reaction tube having a height of 400 mm and an inner diameter of 25 mm in such a way that the catalyst layer length was 100 mm. The catalyst was packed in the reaction tube at room temperature, and the reaction tube was immersed in a heated bath of a molten nitrate salt. After packing the catalyst, a reactant gas having the composition shown in the following reactant gas composition (A) was introduced into the stainless steel reaction tube at a space velocity of 2000 $h^{-1}$ (STP) to carry out vapor phase catalytic oxidation reaction of acrolein. The reaction temperature was 230° C.

Reactant Gas Composition (A)

| | |
|---|---|
| Acrolein | 5% by volume |
| Oxygen | 5% by volume |
| Water vapor | 40% by volume |
| Nitrogen | 50% by volume |

For each of the catalysts (2) to (20), vapor phase catalytic oxidation reaction of acrolein in a single layer was carried out in the same manner as the above, and the acrolein conversion rate of each of the catalysts (1) to (20) was calculated. That is, the catalytic activity in Table 1 means the acrolein conversion rate when the vapor phase catalytic oxidation reaction of acrolein is carried out in each catalyst single layer under the above conditions. The acrolein conversion rate (ACR conversion rate) is calculated by the following expression:

Acrolein conversion rate(mol %)=(Number of moles of acrolein reacted/Number of moles of acrolein supplied)×100

TABLE 1

| Catalyst | Metal element composition of catalytically active component | Amount of Cu [vs.12Mo | Specific surface area [$m^2/g$] | Average diameter of support [mm] | Supporting rate [% by mass] | Catalytic activity: ACR conversion rate [mcl %] |
|---|---|---|---|---|---|---|
| 1 | $Mo_{12}Cu_{1.5}V_{5.5}W_{1.2}Sb_{0.5}Al_{17.6}$ | 1.5 | 7.7 | 8 | 30 | 78.8 |
| 2 | $Mo_{12}Cu_{1.5}V_{5.5}W_{1.2}Sb_{0.5}$ | 1.5 | 9.9 | 5 | 30 | 92.5 |
| 3 | $Mo_{12}Cu_{1.5}V_{5.5}W_{1.2}Sb_{0.5}$ | 1.5 | 9.9 | 5 | 40 | 96.8 |
| 4 | $Mo_{12}V_{2.6}Nb_{1.5}Sb_{1.2}$ | 0.0 | 23.7 | 5 | 23 | 99.8 |
| 5 | $Mo_{12}V_{3.6}Nb_{1.5}Sb_{1.2}$ | 0.0 | 11.3 | 5 | 23 | 95.8 |
| 6 | $Mo_{12}Cu_{0.3}V_{3.6}Nb_{1.5}Sb_{1.2}$ | 0.3 | 27.7 | 5 | 23 | 99.5 |
| 7 | $Mo_{12}V_{3.6}Nb_{1.3}Sb_{1.2}$ | 0.0 | 18.9 | 5 | 23 | 98.9 |
| 8 | $Mo_{12}V_{3.6}Nb_{1.5}Te_{2.0}$ | 0.0 | 19.5 | 5 | 23 | 99.7 |
| 9 | $Mo_{12}V_{3.2}Nb_{1.5}Te_{1.7}$ | 0.0 | 15.1 | 5 | 23 | 98.6 |
| 10 | $Mo_{12}Cu_{0.5}V_{4.2}W_{0.5}Sb_{1.0}$ | 0.5 | 17.6 | 5 | 23 | 98.3 |
| 11 | $Mo_{12}Cu_{0.5}V_{4.2}W_{0.5}Sb_{1.0}$ | 0.6 | 17.5 | 5 | 23 | 98.1 |
| 12 | $Mo_{12}Cu_{0.6}V_{4.2}W_{0.5}Sb_{1.0}$ | 0.8 | 17.3 | 5 | 23 | 97.9 |
| 13 | $Mo_{12}Cu_{1.0}V_{4.2}W_{0.5}Sb_{1.0}$ | 1.0 | 17.2 | 5 | 23 | 97.6 |
| 14 | $Mo_{12}Cu_{0.5}V_{4.2}W_{0.5}Sb_{1.0}$ | 0.5 | 12.9 | 5 | 23 | 94.8 |
| 15 | $Mo_{12}V_{4.5}W_{0.6}$ | 0.0 | 37.5 | 5 | 23 | 99.6 |
| 16 | $Mo_{12}Cu_{0.3}V_{4.5}W_{0.6}$ | 0.3 | 44.8 | 5 | 23 | 99.8 |
| 17 | $Mo_{12}Cu_{3.3}V_{5.5}W_{1.2}Sb_{0.5}Fe_{0.8}$ | 3.3 | 9.6 | 5 | 25 | 83.7 |

TABLE 1-continued

| Catalyst | Metal element composition of catalytically active component | Amount of Cu [vs.12Mo | Specific surface area [m²/g] | Average diameter of support [mm] | Supporting rate [% by mass] | Catalytic activity: ACR conversion rate [mcl %] |
|---|---|---|---|---|---|---|
| 18 | $Mo_{12}Cu_{0.8}V_{5.5}W_{1.2}Sb_{0.5}Fe_{0.5}$ | 0.8 | 10.2 | 5 | 25 | 86.0 |
| 19 | $Mo_{12}Cu_{3.0}V_{3.0}Co_{1.0}Si_{1.0}$ | 3.0 | 8.1 | 5 | 23 | 75.4 |
| 20 | $Mo_{12}Cu_{3.0}V_{3.0}Co_{1.0}Si_{1.0}$ | 3.0 | 8.1 | 5 | 31 | 85.4 |

Examples 1 to 15 and Comparative Examples 1 to 8

<Vapor Phase Catalytic Oxidation Reaction of Acrolein in Multiple Layers>

The catalyst obtained above was packed in a stainless steel reaction tube having a length of 4000 mm and an inner diameter of 25 mm installed in such a way that the tube axis direction was vertical so as to form a catalyst layer having any of the layer height ratios shown in Tables 2 and 3. The packing was carried out while the stainless steel reaction tube was heated using a molten nitrate salt. After the packing, a reactant gas having the composition shown in the following reactant gas composition (B) was introduced into the stainless steel reaction tube at a space velocity of 1800 $h^{-1}$ (STP) to carry out vapor phase catalytic oxidation reaction of acrolein. The layer height of each catalyst layer and the layer height of all the catalyst layers were determined by measuring the space length from the upper end of the reaction tube to the catalyst packed using a measure each time each catalyst was packed. Specifically, a long measure was inserted from the upper end of the reaction tube, and the space length was measured from the graduation when the tip of the measure came into contact with the catalyst.

Reactant Gas Composition (B)

| | |
|---|---|
| Acrolein | 8% by volume |
| Oxygen | 10% by volume |
| Water vapor | 35% by volume |
| Nitrogen | 47% by volume |

[Evaluation]

In the vapor phase catalytic oxidation reaction of acrolein carried out in Examples 1 to 15 and Comparative Examples 1 to 8, the reaction temperature 24 hours after the acrolein conversion rate (ACR conversion rate) reached 99.3 to 99.7% after the start of the reaction (initial reaction temperature), then the reaction temperature when the reaction was continued so as to maintain the acrolein conversion rate at 99.3 to 99.7% and 8000 hours passed, and the acrolein acid yield (AA yield) at each time point were evaluated according to the following methods. The evaluation results are shown in Tables 2 and 3.

Here, the reaction temperature means the temperature of the molten salt as a heat medium, specifically, the temperature of the heat medium in the vicinity of a middle portion of the layer length of all the catalyst layers, and was measured using a type K thermocouple.

The acrylic acid yield (AA yield) is defined by the following expression:

Acrylic acid yield(mol %)=(Number of moles of acrylic acid generated/Number of moles of acrolein supplied)×100

For the initial acrylic acid yield, an acrolein-containing gas was supplied, and the heat medium temperature was adjusted so that the acrolein conversion rate was in the range of 99.3% to 99.7%, and then 24 hours later from that, the composition of a gas discharged from the outlet side was quantitatively analyzed by gas chromatography and the initial acrylic acid yield was calculated from the composition of the gas obtained using the above expression of acrylic acid yield. The acrylic acid yield after 8000 hours was calculated by carrying out the reaction while appropriately regulating the heat medium temperature in such a way that the acrolein conversion rate was within the range of 99.3% to 99.7% and analyzing the composition of a gas discharged from the gas outlet side 8000 hours after supplying the acrolein-containing gas in the same manner as described above.

In the column of "Layer height ratio" in Tables 2 and 3, the types of catalysts and the catalyst layer lengths of the catalysts are listed from left to right in a way separated by "/" in order of disposition from the gas inlet side to the gas outlet side. In the column of "Catalyst having highest activity among catalysts contained in all catalyst layers" in Tables 2 and 3, the features of the catalyst having the highest activity among the catalysts contained in all the catalyst layers is described. When "the catalyst having the highest activity among the catalysts contained in all the catalyst layers" corresponds to the catalyst X according to the present invention (that is, when the catalytically active component has a Cu content of 0.8 mol or less per 12 mol of Mo and a specific surface area of 15 m²/g to 40 m²/g), "yes" is indicated in the column of "Catalyst X" and when "the catalyst having the highest activity" does not correspond to the catalyst X according to the present invention, "no" is indicated in the column of "Catalyst X."

TABLE 2

| | | Catalyst having highest activity among catalysts contained in all catalyst layers | | | | | | |
|---|---|---|---|---|---|---|---|---|
| | Layer height ratio [mm] (gas inlet side/gas outlet side) | Catalyst No. | Metal element composition of catalytically active component | Amount of Cu [vs. 12Mo] | Specific surface area (m²/q) | Catalyst X | Layer height [%] | Supporting rate [%] |
| Comparison Example 1 | (1) 900/(2) 1900 | 2 | $Mo_{12}Cu_{1.5}V_{5.5}W_{1.2}Sb_{0.5}$ | 1.5 | 9.3 | no | 69.7 | 30 |
| Example 1 | (1) 900/(2) 1700/(4) 200 | 4 | $Mo_{12}V_{3.6}Nb_{1.5}Sb_{1.2}$ | 0.0 | 23.7 | yes | 7.1 | 23 |

TABLE 2-continued

| | | | | | | | | |
|---|---|---|---|---|---|---|---|---|
| Comparison Example 2 | (1) 900/(2) 1700/(5) 200 | 5 | $Mo_{12}V_{3.6}Nb_{1.5}Sb_{1.2}$ | 0.0 | 11.3 | no | 7.1 | 23 |
| Example 2 | (1) 1000/(2) 1600/(6) 200 | 6 | $Mo_{12}Cu_{0.3}V_{3.6}Nb_{1.5}Sb_{1.2}$ | 0.3 | 27.7 | yes | 7.1 | 23 |
| Example 3 | (1) 1000/(2) 1600/(7) 200 | 7 | $Mo_{12}V_{2.9}Nb_{1.3}Sb_{3.1}$ | 0.0 | 18.9 | yes | 7.1 | 23 |
| Example 4 | (1) 900/(3) 1700/(8) 200 | 8 | $Mo_{12}V_{3.6}Nb_{1.5}Te_{2.0}$ | 0.0 | 19.5 | yes | 7.1 | 23 |
| Example 5 | (1) 900/(2) 1700/(9) 200 | 9 | $Mo_{12}V_{3.2}Nb_{1.9}Te_{1.7}$ | 0.0 | 15.1 | yes | 7.1 | 23 |
| Example 6 | (1) 900/(2) 1700/(10) 200 | 10 | $Mo_{12}Cu_{0.5}V_{4.2}W_{0.5}Sb_{1.0}$ | 0.5 | 17.8 | yes | 7.1 | 23 |
| Example 7 | (1) 900/(2) 1700/(11) 200 | 11 | $Mo_{12}Cu_{0.6}V_{4.2}W_{0.5}Sb_{1.0}$ | 0.6 | 17.5 | yes | 7.1 | 23 |
| Example 8 | (1) 900/(2) 1700/(12) 200 | 12 | $Mo_{12}Cu_{0.8}V_{4.2}W_{0.5}Sb_{1.0}$ | 0.8 | 17.3 | yes | 7.1 | 23 |
| Comparison Example 3 | (1) 900/(2) 1700/(13) 200 | 13 | $Mo_{12}Cu_{1.0}V_{4.2}W_{0.5}Sb_{1.0}$ | 1.0 | 17.2 | no | 7.1 | 23 |

| | Reaction results | | | |
|---|---|---|---|---|
| | Time elapsed [h] | Reaction temperature [° C.] | ACR conversion rate [%] | AA yield [%] |
| Comparison | Initial | 265 | 99.7 | 93.5 |
| Example 1 | 8000 | 295 | 99.3 | 92.5 |
| Example | Initial | 257 | 99.6 | 94.4 |
| 1 | 8000 | 271 | 99.5 | 94.3 |
| Comparison | Initial | 284 | 99.5 | 93.1 |
| Example 2 | 8000 | 294 | 93.5 | 92.1 |
| Example | Initial | 258 | 99.3 | 94.0 |
| 2 | 8000 | 274 | 99.6 | 94.0 |
| Example | Initial | 261 | 98.3 | 94.2 |
| 3 | 8000 | 283 | 99.3 | 93.4 |
| Example | Initial | 258 | 99.7 | 94.7 |
| 4 | 8000 | 273 | 99.3 | 94.6 |
| Example | Initial | 262 | 99.3 | 94.4 |
| 5 | 8000 | 285 | 99.5 | 93.4 |
| Example | Initial | 262 | 99.7 | 93.7 |
| 6 | 8000 | 283 | 99.3 | 92.6 |
| Example | Initial | 262 | 99.5 | 93.6 |
| 7 | 8000 | 285 | 99.3 | 92.6 |
| Example | Initial | 262 | 99.5 | 93.5 |
| 8 | 8000 | 288 | 995 | 92.5 |
| Comparison | Initial | 262 | 99.6 | 93.2 |
| Example 3 | 8000 | 289 | 99.6 | 92.2 |

TABLE 3

| | | Catalyst having highest activity among catalysts contained in all catalyst layers | | | | | | |
|---|---|---|---|---|---|---|---|---|
| | Layer height ratio [mm] | Catalyst No. | Metal element composition of catalytically active component | Amount of Cu [vs. 12Mo] | Specific surface area ($m^2/q$) | Catalyst X | Layer height [%] | Supporting rate [%] |
| Comparison Example 4 | (1) 900/(2) 1700/(14) 200 | 14 | $Mo_{12}Cu_{0.5}V_{4.2}W_{0.5}Sb_{1.0}$ | 0.5 | 12.9 | no | 7.1 | 23 |
| Example 9 | (1) 1100/(2) 1500/(15) 200 | 15 | $Mo_{12}V_{4.5}W_{0.6}$ | 0.0 | 37.5 | yes | 7.1 | 23 |
| Comparison Example 5 | (1) 1100/(2) 1500/(16) 200 | 16 | $Mo_{12}Cu_{0.3}V_{4.5}W_{0.6}$ | 0.3 | 44.8 | no | 7.1 | 23 |
| Comparison Example 6 | (1) 900/(2) 1700/(3) 200 | 3 | $Mo_{12}Cu_{1.5}V_{5.5}W_{1.2}Sb_{0.5}$ | 1.5 | 9.9 | no | 7.1 | 40 |
| Example 10 | (1) 1100/(2) 800/(10) 900 | 10 | $Mo_{12}Cu_{0.5}V_{4.2}W_{0.5}Sb_{1.0}$ | 0.5 | 17.6 | yes | 32.1 | 23 |
| Example 11 | (1) 1100/(2) 1000/(10) 700 | 10 | $Mo_{12}Cu_{0.5}V_{4.2}W_{0.5}Sb_{1.0}$ | 0.5 | 17.6 | yes | 25.0 | 23 |
| Example 12 | (1) 900/(2) 1830/(15) 70 | 15 | $Mo_{12}V_{4.5}W_{0.6}$ | 0.0 | 37.5 | yes | 2.5 | 23 |
| Example 13 | (1) 900/(2) 1800/(4) 100 | 4 | $Mo_{12}V_{3.6}Nb_{1.5}Sb_{1.2}$ | 0.0 | 22.7 | yes | 3.6 | 23 |
| Example 14 | (1) 900/(2) 1700/(4) 200/(2) 100 | 4 | $Mo_{12}V_{3.6}Nb_{1.5}Sb_{1.2}$ | 0.0 | 23.7 | yes | 6.9 | 23 |

TABLE 3-continued

| | | | | | | | | |
|---|---|---|---|---|---|---|---|---|
| Example 15 | (1) 500/(2) 1600/(4) 200/(2) 100 | 4 | $Mo_{12}V_{3.6}Nb_{1.5}Sb_{1.2}$ | 0.0 | 23.7 | yes | 7.1 | 23 |
| Comparison Example 7 | (17) 800/(18) 2200 | 18 | $Mo_{12}Cu_{0.8}V_{5.5}W_{1.2}Sb_{1.2}$ | 0.8 | 10.2 | no | 73.3 | 25 |
| Comparison Example 8 | (19) 1400/(20) 1400 | 20 | $Mo_{12}Cu_{3.0}V_{3.0}Co_{1.0}Si_{1.0}$ | 3.0 | 8.1 | no | 50.0 | 31 |

| | Reaction results | | | |
|---|---|---|---|---|
| | Time elapsed [h] | Reaction temperature [° C.] | ACR conversion rate [%] | AA yield [%] |
| Comparison Example 4 | Initial | 264 | 93.7 | 93.4 |
| | 8000 | 296 | 99.3 | 92.3 |
| Example 9 | Initial | 259 | 99.4 | 93.2 |
| | 8000 | 280 | 99.7 | 93.0 |
| Comparison Example 5 | Initial | 258 | 99.5 | 92.6 |
| | 8000 | 293 | 99.3 | 91.9 |
| Comparison Example 6 | Initial | 263 | 99.6 | 93.0 |
| | 8000 | 288 | 99.6 | 92.1 |
| Example 10 | Initial | 250 | 99.6 | 93.5 |
| | 8000 | 277 | 99.3 | 92.5 |
| Example 11 | Initial | 262 | 99.5 | 93.7 |
| | 8000 | 278 | 99.5 | 92.6 |
| Example 12 | Initial | 264 | 99.3 | 93.5 |
| | 8000 | 293 | 99.3 | 92.6 |
| Example 13 | Initial | 263 | 99.7 | 93.6 |
| | 8000 | 286 | 99.6 | 92.8 |
| Example 14 | Initial | 257 | 99.7 | 94.2 |
| | 8000 | 271 | 99.7 | 93.8 |
| Example 15 | Initial | 258 | 99.8 | 94.2 |
| | 8000 | 273 | 99.4 | 93.7 |
| Comparison Example 7 | Initial | 282 | 99.3 | 92.5 |
| | 8000 | 290 | 99.4 | 92.4 |
| Comparison Example 8 | Initial | 273 | 99.8 | 93.3 |
| | 8000 | 306 | 99.3 | 92.0 |

As can be seen from Tables 2 and 3, the difference between the initial reaction temperature and the reaction temperature after passing of 8000 hours is small in Examples 1 to 15, which suppresses the degradation of the catalyst over time, and it can be inferred from this that the temperature rise in the catalyst layer is suppressed. In addition, it can be seen in Examples 1 to 15 that the initial yield of acrylic acid is 93.5% or more and that the decrease in the yield of acrylic acid after passing of 8000 hours from the initial yield of acrylic acid is suppressed.

Accordingly, it has been seen that when a catalyst including a catalytically active component x having a particular specific surface area and containing no or a small amount of Cu is provided in the whole or a part of a specific section on the gas outlet side of all the catalyst layers, it is possible to improve the yield of acrylic acid and extend the life of the catalyst.

The present application is based on Japanese Patent Application No. 2020-003870 filed on Jan. 14, 2020, the disclosure of which is incorporated herein by reference in its entirety.

REFERENCE SIGNS LIST

10: reaction tube of fixed bed reactor
11: catalyst layer foremost end
12: catalyst layer rearmost end
21: all catalyst layers
22: catalyst layer including a different type of a catalyst from the catalyst X
23: catalyst layer including catalyst X
24: catalyst layer including catalyst of type different from catalyst X
31: section up to 30% of the length of all catalyst layers from the catalyst layer rearmost end toward the gas inlet side
L: end of section 31

The invention claimed is:

1. A method d for producing acrylic acid, comprising supplying a gas containing acrolein to a fixed bed reactor including a reaction tube to produce acrylic acid by vapor phase catalytic oxidation of acrolein, wherein the reaction tube is packed with catalysts having different activities in such a way that two or more catalyst layers are formed in a tube axis direction of the reaction tube;

a catalyst X having the highest activity among the catalysts contained in all the catalyst layers is placed in the whole or a part of a section up to 30% of a length of all the catalyst layers from a rearmost portion on a gas outlet side toward a gas inlet side of all the catalyst layers;

a layer length of a catalyst layer including the catalyst X is 3 to 30% of the length of all the catalyst layers;

a catalytically active component x in the catalyst X has Mo, V, and optionally Cu, and when Cu is included, an amount thereof is 0.8 mol or less per 12 mol of Mo; and a specific surface area of the catalytically active component x is 15 $m^2/g$ to 40 $m^2/g$.

2. The method for producing acrylic acid according to claim 1, wherein a composition of the catalytically active component x is represented by the following general formula (1), provided that oxygen in an oxidation state is omitted:

$$Mo_{12}Cu_aV_bA_cB_dC_eD_fE_g \quad (1)$$

wherein Mo is molybdenum, Cu is copper, V is vanadium, A is at least one element selected from niobium, tungsten, and tantalum, B is at least one element selected from antimony and tellurium, C is at least one element selected from chromium, manganese, iron, cobalt, nickel, zinc, bismuth, tin, thallium, and a rare earth element, D is at least one element selected from an alkali metal and an alkaline earth metal, E is at least one element selected from silicon, aluminum, titanium, zirconium, and cerium, and a, b, c, d, e, f, and g represent the numbers of atoms of Cu, V, A, B, C, D, and E, respectively, and $0 \leq a \leq 0.8$, $2 \leq b \leq 10$, $0 \leq c \leq 12$, $0 \leq d \leq 6$, $0 \leq e \leq 12$, $0 \leq f \leq 5$, and $0 \leq g \leq 50$.

3. The method for producing acrylic acid according to claim 1, wherein the amount of Cu in the catalytically active component x is 0.6 mol or less per 12 mol of Mo.

* * * * *